(12) United States Patent
Ghirri et al.

(10) Patent No.: US 6,352,974 B1
(45) Date of Patent: Mar. 5, 2002

(54) ORAL CALCITONIN PHARMACEUTICAL COMPOSITIONS AND METHODS OF MAKING THE SAME

(75) Inventors: Matteo Ghirri, Milan; Marco Zema, Como, both of (IT)

(73) Assignee: Eurand International S.p.A. (IT)

( * ) Notice: Subject to any disclaimer, the term of this patent is extended or adjusted under 35 U.S.C. 154(b) by 0 days.

(21) Appl. No.: 09/297,795

(22) PCT Filed: Nov. 5, 1997

(86) PCT No.: PCT/EP97/06104

§ 371 Date: Sep. 21, 1999

§ 102(e) Date: Sep. 21, 1999

(87) PCT Pub. No.: WO98/19697

PCT Pub. Date: May 14, 1998

(30) Foreign Application Priority Data

Nov. 7, 1996 (GB) .............................................. 9623205

(51) Int. Cl.⁷ .............................................. A61K 38/00
(52) U.S. Cl. ........................ 514/12; 514/773; 514/774; 424/422; 424/426; 424/457; 424/458
(58) Field of Search .................................. 424/426, 422, 424/457, 458; 514/774, 773, 12

(56) References Cited

U.S. PATENT DOCUMENTS 5,021,241 A * 6/1991 Yamahira ..................... 424/426

FOREIGN PATENT DOCUMENTS

| DE | 4119140 | * 12/1992 |
| EP | 0399781 | 11/1990 |
| GB | 2176105 | * 12/1986 |
| JP | 8225454 | 9/1996 |

* cited by examiner

Primary Examiner—F. T. Moezie
(74) Attorney, Agent, or Firm—Thompson Hine LLP

(57) ABSTRACT

The present invention relates to novel compositions, in particular to compositions comprising calcitonin or a fragment or conjugate thereof and to methods for preparing such compositions. It also relates to oral formulations comprising the compositions and to shelf stable formulations of calcitonin or a fragment or conjugate thereof.

7 Claims, No Drawings

ORAL CALCITONIN PHARMACEUTICAL COMPOSITIONS AND METHODS OF MAKING THE SAME

FIELD OF THE INVENTION

The present invention relates to novel compositions, in particular to compositions comprising calcitonin or a fragment or conjugate thereof and to methods for preparing such compositions. It also relates to oral formulations comprising the compositions and to shelf stable calcitonin or a fragment or conjugate thereof.

Many proteins and polypeptides have potential as pharmaceutical agents but because they are susceptible to both physical and chemical degradation they are often too unstable to be included in pharmaceutical formulations. In particular such proteins and polypeptides do not have adequate shelf life.

The primary, secondary and tertiary structures of proteins and polypeptides are all vulnerable to various types of disruption. Some proteins and peptides are physically unstable as a result of, for example, adsorption, aggregation or denaturation. Others are chemically unstable as a result of, for example, oxidation, hydrolysis, deamidation, beta-elimination, racemisation or disulphide exchange (if the polypeptide contains a disulphide bridge e.g. a cystine link). Many proteins and polypeptides are susceptible to a number of these factors.

In order to formulate proteins and polypeptides into pharmaceutical preparations the factors described above must be taken into consideration. Thus proteins and peptides often have more complex formulation requirements than chemical pharmaceuticals. This is further complicated by the fact that many stages in the processing of pharmaceutical formulations introduce further stresses on the proteins and polypeptides which destabilise them. For example, processes such as heating, shaking, freeze thawing and processes in which the proteins or polypeptides are exposed to hydrophobic surfaces or to moisture may induce aggregation of the protein or polypeptide. Aggregation may also occur during the storage of the formulation, particularly if it is exposed to moisture.

Various excipients such as albumin, amino acids, sugars, chelating agents, cyclodextrins and polyhydric alcohols, have been added to proteins and polypeptide pharmaceutical formulations in order to increase their stability. These have been of varying success depending on the protein or polypeptide concerned. The excipients stabilise the proteins and polypeptides in different ways, not all of which are fully understood, for example, albumin is added to prevent surface adsorption of pharmaceuticals by preferentially adsorbing to surfaces, whilst amino acids are added to reduce surface adsorption, to inhibit aggregation or to reduce heat degradation. Sugars are added to provide stability during processes such as heating and lyophilisation.

BACKGROUND OF THE INVENTION

Although the use of excipients to stabilise proteins and polypeptides has proved suitable for the stabilisation of some proteins and polypeptides it is inadequate for the stabilisation of less stable proteins and polypeptides, particularly those containing a disulphide bridge, such as a cystine link, e.g. calcitonin. There is therefore a need for further methods of stabilising proteins and polypeptides which are capable of stabilising these less stable proteins and polypeptides. In particular there is a need for a method of stabilising polypeptides with a disulphide bridge, e.g. calcitonin. The present invention utilises the techniques of freeze drying to provide such a method.

Proteins and polypeptides have previously been lyophilised (e.g. by freeze drying) in order to prepare powders which may be stored and reconstituted when required. The proteins and polypeptides are freeze dried in the presence of cryoprotectants and lyoprotectants (e.g. sugars, polyols, polymers such as polyethylene glycol, amino acids and organic salts such as sodium acetate) which are required to prevent the denaturation of the protein or polypeptide.

This technique is not suitable for all proteins and polypeptides, in some cases the cryoprotectants and lyoprotectants induce conformational instability to the proteins or polypeptides to be lyophilised or the freeze dried product has been found to be susceptible to degradation.

Thus, some proteins and polypeptides have been freeze dried in the presence of cryoprotectants and lyoprotectants but these techniques have not before been utilised to prepare solid oral preparations of unstable proteins or polypeptides such as those having a disulphide bridge. In particular these techniques have not before been utilised to provide a stable oral formulation of calcitonins. Furthermore, the known techniques relate only to the stabilisation of aqueous preparations of proteins and polypeptides to provide injectable or nasal dosage forms and do not provide solid dosage forms.

Calcitonins are hypocalcemic hormones found in the thyroid, parathyroid and thymus glands of man and in separate organs called ultimobranchial bodies in non-mammalian vertebrates. During hypercalcemia calcitonins reduce elevated plasma calcium concentration to normal levels by inhibiting bone resorption. Calcitonins are therefore used to treat a variety of conditions such as Paget's disease, post menopausal osteoporosis and also to treat hypocalcemia resulting from vitamin D intoxication, neoplastic disease, thyrotoxicosis or hyperthyroidism.

Salmon calcitonin is a polypeptide with a molecular weight of 3431.9 which consists of 32 amino acids. It has a disulphide bridge (cystine link) between the first and seventh amino acids at the amino end of the polypeptide chain, which is essential for its biological activity, and a prolinamide group at the carboxyl terminal amino acid. The presence of this disulphide bridge contributes to the lack of stability of calcitonin because, under thermal stress, it is susceptible to beta-elimination to produce free thiols. These thiols render the molecule vulnerable to degradation via various pathways and may also increase the occurrence disulphide interchanges thus affecting the conformation and therefore the activity of the polypeptide.

Calcitonins are currently only available in solution and are administered by intravenous infusion, by intramuscular injection, subcutaneously or intranasally. In order to maintain biological activity pharmaceutical preparations containing calcitonin must be stored at a temperature of 2 to 8° C. Storage at low temperatures slowing down the extent of degradation which occurs at a high rate in the liquid phase.

It is widely recognised in the pharmaceutical industry that oral drug delivery is the preferred mode of drug administration. Whether the pharmaceutical is administered by the patient or by a medical practitioner oral administration is simpler than invasive methods of administration. Oral administration is generally more acceptable to patients and so increases patient compliance. Oral administration also avoids the need to use sterilised equipment such as syringes when administering the pharmaceutical, which results in increased safety for the patient.

The preparation of solid pharmaceuticals is simpler and cheaper than the preparation of pharmaceuticals in the form of a solution. This is particularly the case where the solution is an injectable solution or an internasal spray. In contrast to oral pharmaceutical formulations injectable pharmaceutical solutions must be prepared in sterile conditions in highly regulated laboratories. This is necessary because pharmaceuticals administered by injection are delivered directly into the blood stream or the muscles of the patient, so even a small amount of contamination could cause significant adverse effects. Pharmaceuticals which are administered in solid oral dosage forms are ingested and pass through the alimentary canal before the active component is released into the blood stream or into the tissues of the patient. Thus small amounts of contamination will be excreted by the body during the normal digestive process. The requirement to prepare pharmaceutical solutions under highly sterile conditions increases the cost and inconvenience of their preparation.

Although solid oral dosage forms are desirable, their provision is not always possible. In the case of polypeptides such as calcitonins the provision of solid oral dosage formulations is hindered by the high instability of the polypeptides. These materials are not suitable for processing into a solid dosage forms because they cannot withstand the physical and chemical stresses of conventional formulating techniques. There is therefore a need for calcitonin in a solid dosage form, more particularly there is a need for a solid oral dosage form of calcitonin. There is a further need for calcitonin in a solid dosage form with an improved shelf life, more preferably one which will not have to be stored at low temperatures.

There is a further need for solid dosage formulations of proteins or polypeptides in which the protein or polypeptide is homogeneously distributed throughout the formulation. This allows an accurate amount of pharmaceutical to be administered, which is particularly important for potent pharmaceuticals, such as calcitonin, in which any deviation from the desired dose would be significant in its effects. Porcine and human calcitonins typically have an activity of 100 to 200 IU/mg and salmon calcitonins typically have an activity of up to 6500 IU/mg.

There is also a need for solid compositions containing a homogeneous distribution of calcitonin which are-useful to prepare the solid dosage formulations described above.

Gelatin is a material obtained by the partial hydrolysis of collagen, a fibrous protein found in animal bones, skin and conjunctive tissue. It is widely used in the food industry, for example as a foaming agent or a binding agent. It is also widely used in the adhesive industry and in the photographic industry where it plays an important role in all stages of photographic film manufacture. Gelatin is also widely used in the pharmaceutical industry where its properties (particularly its gelling properties) make it an ideal material from which to manufacture both soft and hard capsules.

It is generally accepted that the most important properties of gelatin are its ability to form gels at room temperature and its amphoteric nature. The ability of different gelatins to form gels is measured by the Bloom number (measured in accordance with association of Official Analytical Chemists (AOAC) and British Standards), which is often used to characterise different gelatins. The gelling property of gelatin is related to the chain lengths of the polypeptides it contains. Gelatins having larger polypeptides have improved gelling properties. Gelatins have been fractionated and the fractions containing the larger polypeptides used for their improved gelling properties. The fractions containing smaller polypeptides are generally considered to be less useful as they have poor, if any, gelling ability.

Gelatins may be produced by acid, base or enzyme hydrolysis of collagen. Gelatins prepared by acid hydrolysis are termed Type A gelatins and those prepared by base hydrolysis are termed type B gelatins. These gelatins differ in their isoelectric points and owe their different properties to the methods by which they are produced rather than the source of collagen from which they are derived. The present invention utilises hydrolysed gelatin of either type, regardless of it's isoelectric point.

Hydrolysed gelatins are mixtures of the hydrolysis products of gelatin. They comprise a mixture of polypeptides of varying sizes, depending on the extent of hydrolysis. They can be characterised by the average molecular weight of the peptides of which they are comprised.

Hydrolysed gelatins are quite distinct from gelatin, in particular they are devoid of gelling properties and therefore have no Bloom number. Furthermore they can be dissolved in water at room temperature whereas gelatin can only be dissolved in water on heating. Gelatin slowly swells and softens when immersed in water at room temperature, gradually absorbing five to ten times as much water as its own weight.

DETAILED DESCRIPTION OF THE INVENTION

The present invention provides a solid composition comprising calcitonin or a conjugate or fragment thereof and gelatin characterised in that the gelatin is hydrolysed gelatin or low molecular weight gelatin and the composition is obtainable by freeze drying a homogeneous aqueous solution comprising the calcitonin, fragment of conjugate thereof and hydrolysed gelatin or low molecular weight gelatin. The gelatin is preferably hydrolysed gelatin.

The molecular weight of the polypeptide fragments making up the hydrolysed gelatin can be measured by gel permeation chromatography. The average molecular weight of the hydrolysed gelatin can then be expressed as NAMW or as WAMW as described in U.S. Pat. No. 5,120,761. The hydrolysed gelatin utilised in the present application preferably has a mean molecular weight (expressed as WAMW) from about 1000 to about 15000 Daltons, more preferably from about 3000 to about 12000 Daltons, most preferably from about 5000 to about 10000 Daltons.

The composition preferably comprises a concentration of gelatin from about 0.01% to about 30% weight/weight of the aqueous solution, e.g. from about 5% to about 20% weight/weight of the aqueous solution or from about 10% to about 20% weight/weight of the aqueous solution. The composition most preferably comprises a concentration of gelatin from about 13% to about 20% weight/weight of the aqueous solution.

The hydrolysed gelatin incorporated in the composition of this invention has substantially no gelling properties at room temperature, that is, when 30% or less of the hydrolysed gelatin is added to water at room temperature it forms a solution rather than a gel. This contrasts with the properties of gelatin, which forms a gel at room temperature even at concentrations as low as 1%. Gelatins are characterised by their gel forming properties, e.g. by their Bloom Number. In contrast to this hydrolysed gelatins have a Bloom Number of zero because they do not readily form gels under usual laboratory conditions, e.g. at 20° C.

Hydrolysed gelatins are commercially available. Hydrolysed Type A and/or B gelatins may be used in the present invention. The hydrolysed gelatin particularly preferred is that supplied by Sanofi Bioindustries, 18 Via Bovisasca, I-20026 Novate Milanese (Hydrolysed Gelatin ASF type A or B ).

A low molecular weight gelatin may be utilised in the invention. This is a gelatin having a mean molecular weight from about 1000 to about 15000 Daltons, more preferably from about 3000 to about 12000 Daltons, most preferably from about 5000 to about 10000 Daltons. Low molecular weight gelatin may suitably be obtained by fractionating gelatin and using the low molecular weight fractions.

Freeze drying may suitably be performed using conventional freeze drying apparatus. Further details of the freeze drying methods and preferred conditions for performing the present invention are discussed below.

The calcitonin may be a naturally occurring calcitonin such as salmon, eel, porcine or human calcitonin or a synthetic calcitonin such as those having at least 70% homology with the aforementioned naturally occurring calcitonins. Preferred synthetic calcitonins are those with at least 80% homology with natural calcitonins. More preferred are those with at least 90% homology and most preferred are those with at least 95% homology to the natural calcitonins. Particularly preferred embodiments of the present invention comprise salmon calcitonin, more particularly totally synthetic salmon calcitonin.

The calcitonin may suitably be conjugated to a hydrophilic or hydrophobic polymer, e.g. to a polyalkylene glycol moiety. One suitable method of preparing a conjugate of calcitonin is described in U.S. Pat. No. 5,359,030. Alternatively a fragment of the calcitonin may be used.

As calcitonin is stable in an aqueous solution with a pH of about 3.3 to about 6.0, a solution of hydrolysed gelatin which has a pH value of about 5.0 to about 6.0 provides a solution in which calcitonin can suitably be dissolved without the need of a buffer. However, if desired buffers could be added to lower the degradation of calcitonin in the liquid phase prior to freeze drying.

The ratio of calcitonin to gelatin used in the present invention is typically from about 0.1:1000 to about 10:1000 weight by weight, preferably from about 0.5:1000 to about 5:1000 weight by weight, more preferably from about 0.8:1000 to about 1:1000 weight by weight.

The composition of the present invention may suitably be obtained as solid cake. If necessary the solid may be milled and/or sieved as required to provide a particulate solid e.g. granules or a powder. The material prepared is eminently suitable for further processing into an oral pharmaceutical or veterinary medicine. This semi-finished material can be further processed to provide a variety of final pharmaceutical or veterinary preparations by conventional methods. Alternatively suitable excipients may be added to the aqueous solution of calcitonin, fragment or conjugate and hydrolysed or low molecular weight gelatin prior to freeze drying. The desired formulation can then be formed directly during the freeze drying process, e.g. the solution can be added to a mould having tablet shaped cavities so as to form tablets during the freeze drying process.

The solid freeze dried semi-finished product obtained comprises calcitonin, fragment or conjugate homogeneously dispersed in a matrix of hydrolysed gelatin, which may suitably be divided into dose units of equal activity. This is advantageous because it allows the administration of an accurate dose of calcitonin, fragment or conjugate. This is particularly important for the administration of potent pharmaceuticals such as calcitonin because any deviation from the required dose has significant effects.

The present invention further provides an oral pharmaceutical formulation comprising a solid composition as described above, optionally with further pharmaceutically acceptable carriers. This formulation may suitably be in the form of tablets, capsules, granules, pellets, a powder, an effervescent solid, a chewable solid formulation, a buccal formulation or a formulation comprising minitablets. As calcitonin is susceptible to gastric degradation the formulation should be enteric coated to provide gastric protection. If desired it may also be coated so as to provide slow release of the calcitonin.

One preferred embodiment of the invention provides a buccal pharmaceutical preparation comprising a solid composition as described above. A further preferred embodiment provides a pharmaceutical preparation comprising coated granules or minitablets which comprise a solid composition as described above to provide delayed and/or sustained release of the calcitonin, fragment or conjugate. Particularly preferred is a sustained release formulation as described in EP 524989 in which the minitablet comprises a composition as described above.

The activity of the material will depend on the particular calcitonin, fragment or conjugate concerned. The oral pharmaceutical preparations of the invention preferably comprise synthetic calcitonin and have a unit dose of active material from about 20 to about 600 I.U., more preferably from about 50 to about 400 I.U., or from about 90 to about 150 I.U., most preferably from about 100 to about 150 I.U.

The activity of the material can be determined by HPLC, e.g. following the technique described in "A validated HPLC assay for salmon calcitonin analysis; R. H. Buck and F. Maxl; Analytical Research and Development and Quality Assurance, Sandoz Pharma Ltd, CH-4002 Basle."

The present invention particularly provides shelf stable compositions comprising calcitonin or a fragment or conjugate thereof. Preferred compositions are those which can be stored for nine months at a temperature of about 20 to about 30° C. and a relative humidity of about 50% to about 65% and retain at least 90% active calcitonin, fragment or conjugate (compared to the amount originally present). More preferably they are able to retain at least 95% active calcitonin, fragment or conjugate over this period and in these conditions. Most preferably they are able to retain at least 96% active calcitonin, fragment or conjugate over this period and in these conditions.

Preferred embodiments of the invention are those which can also withstand more extreme conditions than those described above. Such embodiments include those which can be stored for six months at a temperature of about 35 to about 45° C. and a relative humidity of about 70 to about 80% and retain at least 90% active calcitonin, fragment or conjugate The present invention also provides a homogeneous solution comprising calcitonin or a fragment or conjugate thereof and hydrolysed gelatin or low molecular weight gelatin which can be used to prepare the compositions described above. The gelatin included is preferably that described above.

A further aspect of the present invention provides methods for the preparation of the compositions described above comprising freeze drying a homogeneous aqueous solution comprising calcitonin or a fragment or conjugate thereof and hydrolysed gelatin or low molecular weight gelatin. The gelatin included is preferably that described above.

The homogeneous solution of calcitonin, fragment or conjugate and hydrolysed gelatin is prepared, preferably at room temperature, by dissolving the desired quantities of calcitonin, fragment or conjugate and hydrolysed gelatin in water and combining the solutions formed. Alternatively the gelatin or the calcitonin, fragment or conjugate may first be dissolved in water and the other added in solid form.

The product may suitably be milled and/or sieved as required to provide a particulate solid e.g. granules or a powder. Excipients can be added to this material and it may be further processed into an oral pharmaceutical or veterinary medicine.

Alternatively suitable excipients may be added to the calcitonin, fragment or conjugate and hydrolysed or low molecular weight gelatin prior to freeze drying and a desired formulation formed directly during the freeze drying process, e.g. the solution can be added to a mould having tablet shaped cavities so as to form tablets during the freeze drying process. This would have the advantage of preparing the final dosage form within a single process without the need for further formulation steps after freeze drying. This could lead to increased efficiency in the preparation of the dosage form and a reduction in costs. A further advantage of adding excipients to the solution before it is freeze dried is that a material with a small proportion of excipients but a high active principle content can be produced. This enables smaller tablets with high activity to be prepared, which is advantageous because it increases patient compliance and further reduces the costs of preparing the formulation.

As calcitonin is stable in an aqueous solution with a pH of about 3.3 to about 5.5, a solution of hydrolysed gelatin which has a pH of about 5.0 to about 6.0 provides a solution in which calcitonin can suitably be dissolved without the need of a buffer. However, if desired buffers could be added to optimise the dissolution of the materials.

Freeze drying may be achieved by a three stage process involving freezing, primary drying and secondary drying, using conventional apparatus. For example vials or trays containing the solution to be freeze dried are placed in a freeze dryer, which typically comprises a chamber connected to a vacuum pump, a condenser and a refrigeration system. Some freeze dryers may also include a means of filling or sterilising the vials and/or a means for controlling or automating some aspects of the freeze drying process by setting time, pressure and temperature. During the freeze drying process the water (or other solvent) content is conveniently removed from a frozen solution by sublimation.

In a typical process the solution to be freeze dried is first frozen in the freeze dryer by reducing the chamber temperature. Once the material is completely frozen a vacuum is applied and the temperature of the shelves is increased. In this way the frozen water is removed under vacuum through sublimation, in what is called the primary drying stage. Once all the frozen water is removed the product will appear to be dry, although it will contain some bound unfrozen water. This is then removed by further increasing the temperature of the shelves during what is called the secondary drying stage. A rise in product temperature can be observed during this stage because heat of sublimation is no longer required. This increase in temperature can be used as an indicator that secondary drying is almost complete.

The nature of the product obtained by freeze drying may be modified by adjusting the conditions under which the material is freeze dried, e.g. by adjusting the temperature or vacuum applied or by altering the length of time for which the material is freeze dried. Suitable conditions for the performance of the present invention will be apparent to a skilled person, but an example of such suitable conditions is discussed below.

One particularly suitable method of freeze drying is to add a homogeneous solution of hydrolysed gelatin and calcitonin or a fragment or conjugate thereof to trays so that the depth of the liquid is about 1.5 cm. The trays are then placed onto shelves of a freeze drying apparatus at room temperature. The temperature of the shelves is then lowered to a desired value, (e.g. to about −50° C.) at atmospheric pressure and maintained at this temperature for a sufficient length of time (e.g. for 5 hours) to ensure that the solution is completely frozen.

Once the solution is frozen a vacuum (e.g. 0.1 mbar) is applied and the temperature maintained at −50° C. for about 30 to 60 minutes to allow condenser cooling and chamber vacuum optimising.

The temperature of the shelves is then gradually increased to about 20° C. (e.g. in about 4 hours) to facilitate primary drying. The temperature of the shelves is maintained for a further period (e.g. for about 24 to 48 hours) to allow the completion of primary drying. The temperature of the shelves is then further increased to about 27° C. (e.g. in about 10 minutes) and maintained over a period of about 4 to 6 hours to facilitate the secondary drying of the material. During this phase the vacuum level tends to reach low values such as 0.03 mbar due to the water evaporating rate reduction. The product obtained may be discharged after raising the chamber pressure to atmospheric value.

One advantage of the present invention is that it does not require the addition of any cryoprotectants or lyoprotectants to the solution prior to freeze drying. As discussed above these additives are generally regarded as essential during the freeze drying of natural products to prevent their degradation. The use of excipients in methods of the present invention is not essential and are only included if desired. The methods of the present invention are preferably also simpler and therefore less expensive than known methods.

A further advantage of the present invention is that the solid formulation can be prepared by dissolving the calcitonin, fragment or conjugate in an aqueous solution of hydrolysed or low molecular weight gelatin at room temperature. This avoids the use of elevated temperatures which are necessary in many formulation processes, which would not be appropriate in the formulation of thermolabile proteins and polypeptides such as calcitonins, which would be degraded during such a process.

The present invention will now be exemplified with reference to the following Examples, by way of illustration only.

EXAMPLES

Example 1

The Preparation of Freeze Dried Powders Comprising Calcitonin 15.0 g of hydrolysed gelatin ASF type B, obtained from Sanofi Bioindustries (Via Bovisasca 18, Novate Milanese (Mi) I-20026) was dissolved in 100.0 g of purified water in a beaker equipped with stirring apparatus. 0.012 g of salmon calcitonin (potency 6567.7 I.U./mg) was then added and the solution formed loaded onto trays so that the depth of the liquid was about 1.5 cm. The solution was then freeze dried in accordance with the following freeze drying procedure detailed be low in table 1:

TABLE 1

FREEZE DRYING PROCEDURE

| STAGE | SHELF TEMPERATURE (° C.) | VACUUM GRADE (mbar) | TOTAL TIME ELAPSED (hrs:mins) |
|---|---|---|---|
| loading | +20 | 1033 | 00.01 |
| freezing | −50 | 1033 | 05.01 |
| condenser cooling | −50 | 1033 | 05.31 |
| vacuum evacuation | −50 | 1033 -> 0.1 | 06.01 |
| primary drying | −50 -> +20 | 0.1 | 10.01 |
| primary drying | +20 | 0.1 | 48.01 |
| secondary drying | +20 -> +27 | 0.1 | 48.31 |
| secondary drying | +27 | 0.1 | 52.01 |
| discharge | +27 | 0.1 -> 1033 | 52.06 |

The homogeneous solution prepared was added to trays so that the depth of the liquid was no greater than 1.5 cm deep. The trays were placed onto freeze dryer shelves set at room temperature. The temperature of the shelves was lowered to about −50° C. and maintained this level for about five hours to ensure the solution was completely frozen.

Condenser cooling and vacuum evacuation was then achieved by applying a vacuum of about 0.1 mbar. The temperature of the shelves was then raised to about 20° C. over a period of about 4 hours to allow the primary drying to take place. The temperature and pressure were maintained at these levels for a further 38 hours to complete the sublimation process.

The temperature was then increased to about 27° C. over about 30 minutes and maintained at this level for about 3 hours 30 minutes to allow the completion of the secondary drying. The dried product obtained was discharged after restoring the chamber pressure to atmospheric value. The product was then sieved using a screen with 1250 μm net openings to provide a salmon calcitonin powdery composition with a potency of 0.8 mg/g.

This procedure was repeated three times replacing the hydrolysed gelatin type B with hydrolysed gelatin type A, mannitol and glycine respectively. The preparations formed also had a potency of 0.8 mg/g. All four preparations were subjected to storage stability trials as described below in Example 3.

Example 2

The Preparation of a Granular Composition Comprising Calcitonin 427.8 g of lactose, was granulated with an aqueous solution composed of:

| | |
|---|---|
| 0.121 g | Salmon calcitonin |
| 11.000 g | PEG |
| 1.100 g | Potassium phosphate monobasic |
| 54.100 g | Purified water | sufficient phosphoric acid to adjust the pH to 4

The granular product obtained was dried and sieved using a screen with 500 μm net openings. The salmon calcitonin potency in the granular composition was 0.275 mg/g. This preparation was subjected to stability trials as described below in Example 3.

Example 3

Comparison of the Storage Stability of the Preparations Prepared According to the Methods of Examples 1 and 2

Two sets of each of the preparations described above in Examples 1 and 2 were prepared according to the methods described therein.

One set of preparations was then stored at a temperature of 25° C. and a relative humidity (R.H) of 60% and the other set was stored at a temperature of 40° C. and a relative humidity of 75%. The stability of the salmon calcitonin comprised in each of these preparations was then determined at different periods of time of storage by measuring the active calcitonin content after storage (by HPLC techniques) and the active calcitonin content before the storage to determine the residual activity (%). The results obtained are shown below in Table 2.

TABLE 2

A COMPARISON OF THE STORAGE STABILITY OF VARIOUS PREPARATIONS OF CALCITONIN

Residual activity (%) of salmon calcitonin
Conditions:

| | 25° C. + 60% R. H. | | | | 40° C. + 75% R. H. | | | |
|---|---|---|---|---|---|---|---|---|
| Time: | 1° month | 2° month | 3° month | 6° mth | 1° week | 1° month | 2° month | 6° month |
| Example 1: Hydrolysed Gelatin Type B | 100 | 99.6 | — | 97.1 | — | 96.3 | 96.3 | 91.9 |
| Example 1: Hydrolysed Gelatin Type A | 100 | — | — | 97.3 | — | 96.0 | 96.7 | 90.2 |
| Example 1: Mannitol | — | — | — | — | 57.0 | — | — | — |
| Example 1: Glycine | — | — | — | — | 37.5 | — | — | — |
| Example 2: granulated product | 54.6 | 49.2 | 47.9 | — | 74.0 | — | — | — |

As shown above in Table 2 the compositions prepared by freeze drying calcitonin with hydrolysed gelatin (both Type A and Type B) shows improved stability with respect to heat and humidity compared to similar preparations obtained using mannitol or glycine. The results also show improved stability of the compositions prepared by freeze drying calcitonin with hydrolysed gelatin (both Type A and Type B) with respect to heat and humidity compared to the granular preparation prepared according to the method of Example 2.

Example 4
The Preparation of a Buccal Composition Comprising Freeze Dried Calcitonin A mixture composed of:
2000 g of active freeze dried powder having a salmon calcitonin potency of 5.25 I.U./mg prepared according to Example 1 and utilising hydrolysed gelatin Type B
10885 g of fillers,
1500 g of binders
100 g of absorption enhancer
15 g of sweetening agent,
500 g of lubricants was prepared and was then compressed utilising a rotary tabletting machine equipped with punches having a diameter of 8.2 mm and a curvature radius of 5.75 mm.

100000 tablets are obtained in this way, each having a weight of 150 mg and a content of salmon calcitonin of 105 I.U.

Example 5
The Preparation of a Minitablet Formulation Comprising Freeze Dried Calcitonin Minitablets were prepared by the following procedure:
Preparation of the Core
A mixture of:
1500 g of active freeze dried powder having a salmon calcitonin potency of 5.25 I.U./mg prepared according to Example 1 and utilising hydrolysed gelatin Type B
16282.5 g of fillers
592.5 g of lubricants was compressed utilising a rotary tabletting machine equipped with punches having a diameter of 2 mm. 75000 doses were obtained each having a weight of 245 mg and a content of salmon calcitonin of 105 I.U.
Preparation of an Inner Coat
17000 g of salmon calcitonin Minitablets were charged into a coating pan and sprayed with an alcoholic solution composed of:
177.0 g of water insoluble polymer mixture
35.4 g of plasticizer
2447.2 g of ethanol
Preparation of an Outer Coat
After drying, the above minitablets were successively sprayed with an alcoholic suspension composed of:
558.0 g of Triethylcitrate
2233.1 g of pH dependant membrane
1116.6 g of Talc
22730.0 g of Ethanol
69390 doses of coated Minitablets are obtained each having a weight of 304.4 mg and a content of salmon calcitonin of 105 I.U.

Example 6
The Preparation of a Compressed Freeze Dried Composition Comprising Calcitonin and Hydrolysed Type a Gelatin
2000 g active freeze dried powder having a salmon calcitonin potency of 5.25 I.U./mg was prepared according to the method described above in Example 1 but hydrolysed gelatin type A was utilised instead of hydrolysed gelatin type B.

This was then combined with the following:
1157.5 g fillers
165 g binders
100 g absorption enhancers
15 g of sweetening agent
500 g of lubricants The resulting composition was compressed utilising a rotary tableting machine equipped with punches having a diameter of 8.2 mm and a curvature radius of 5.75 mm. 26250 tablets were obtained in this way, each having a weight of 150 mg and a content of salmon calcitonin of 400 I.U.

Example 7
The Preparation of a Further Compressed Freeze Dried Composition Comprising Calcitonin and Hydrolysed Type a Gelatin 15.0 g of hydrolysed gelatin ASF type A, obtained from Sanofi Bioindustries, was dissolved in 100 g purified water in a beaker equipped with stirring apparatus. 0.0458 g salmon calcitonin (potency 6567.7 I.U./mg) was added and the solution formed was loaded onto trays and freeze dried in accordance with the freeze drying procedure described above in Example 1.

The following composition was prepared:

10.0 g active freeze dried powder having a calcitonin potency of 20.00 I.U./mg
54.4 g fillers
7.5 g binders
0.5 g absorption enhancers
0.1 g sweetening agent
2.5 g lubricants This composition was compressed utilising a rotary tableting machine equipped with punches having a diameter of 8.2 mm and a curvature radius of 5.75 mm. 500 tablets were obtained in this way, each having a weight of 150 mg and a content of salmon calcitonin of 400 I.U.

Example 8

Demonstration of the Storage Stability of Buccal and Minitablet Formulations of Calcitonin The finished products prepared according to the methods described in Examples 4, 5 and 7 were divided into two sets. One set of each preparation was stored at a temperature of 25° C. and a relative humidity (RH) of 60%. The other set was stored at a temperature of 40° C. and a relative humidity of 75%. The stability of the salmon calcitonin was determined at periods from the start of storage by comparing the active calcitonin content after storage to the active calcitonin content before storage by measuring the residual activity % of salmon calcitonin by HPLC.

The results obtained from this comparison are shown below in Table 3

TABLE 3

DEMONSTRATION OF THE STORAGE STABILITY OF BUCCAL AND MINITABLET PREPARATIONS OF CALCITONIN

| | Residual activity (%) of salmon calcitonin | | | | | |
|---|---|---|---|---|---|---|
| | 25° C. + 60% R. H. | | | 40° C. + 75% R. H. | | |
| Examples | 3° month | 6° month | 9° month | 2° month | 3° month | 9° month |
| Example 4: Buccal formulation. | 100.0 | 99.2 | 97.6 | 99.6 | 91.6 | 52.2 |
| Example 5: Minitablet formulation. | 100.0 | 99.1 | 96.5 | 100.0 | 90.5 | — |
| Example 7: Buccal formulation. | 100.0 | 97.3 | 94.0 | 94.4 | 90.1 | — |

The above results show the calcitonin in the buccal and minitablet formulations is stabilised and that very little degradation occurs after nine months at a temperature of 25° C. and a relative humidity of 60%.

Under the more extreme conditions of a temperature of 40° C. and a relative humidity of 75% the calcitonin is also stabilised. Degradation occurs at a greater rate than at the lower temperature and relative humidity but the calcitonin is still clearly stabilised over a period of months. Even after three months at these extreme conditions over 90% of the calcitonin is still active.

These conditions are much more extreme than the conditions in which pharmaceuticals would normally be stored. These results therefore show that the formulations have improved stability in even extreme conditions. This is an advantage because although one would not normally store pharmaceuticals in these conditions for a period of time, an unexpected and unintentional exposure of the preparations to these conditions would not result in immediate degradation of the product.

Thus the stabilised calcitonin preparations have improved stability under normal storage conditions and are less sensitive to short periods of exposure to extreme conditions. The calcitonin was also shown to be stabilised in the presence of common pharmaceutical excipients.

Example 9
The Preparation of a Fast Melting Tablet Formulation Comprising Freeze Dried Calcitonin The following components are dissolved in 95.4 g of purified water in a beaker equipped with stirring apparatus:

| | |
|---|---|
| 15.00 g | hydrolysed gelatin ASF Type B |
| 1.61 g | filling agents |
| 0.32 g | absorption enhancer |
| 0.17 g | sweetening agent |

0.012 g of salmon calcitonin having a potency of 6250 I.U/mg is dissolved in the solution, which is then added to a mould having tablet shaped cavities (diameter approximately 1 cm). Each cavity is filled with approximately 300 mg of the aqueous solution and the solution is then freeze dried as described in Example 1.

375 fast melting tablets suitable for use in the buccal pouch are obtained in this way, each having a weight of 45.6 mg and a calcitonin content of 200 I.U.

Example 10
The Preparation of a Formulation Comprising Freeze Dried Calcitonin with Hydrolysed Type a Gelatin and Hydrolysed Type B Gelatin 7.5 g hydrolysed gelatin ASF type A and 7.5 g hydrolysed gelatin type B are dissolved in 100 g of purified water in a beaker equipped with stirring apparatus. 0.0458 g Salmon Calcitonin (potency 6567.7. I.U./mg) is added and the solution formed loaded onto trays and freeze dried in accordance with the freeze drying procedure described above in Example 1.

Minitablets are prepared by mixing the hydrolysed gelatin mixture with the following:

10.0 g active freeze dried powder having a calcitonin potency of 20.00 I.U./mg 108.6 g fillers 3.9 g lubricants The mixture is compressed utilising a rotary tableting machine equipped with punches having a diameter of 2 mm to provide 500 doses each having a weight of 245 mg and a content of salmon calcitonin of 400 I.U.

Preparation of the Inner Coat and Outer Coat

The minitablets are spray coated according to the procedure described in Example 5 to provide 500 doses each having a weight of 304.4 mg and a content of salmon calcitonin of 400 I.U.

What is claimed is:

1. An oral pharmaceutical formulation chosen from the group consisting of tablets, minitablets, capsules, granules, pellets, powders, effervescent solids, and chewable solid formulations, said formulation comprising calcitonin or a conjugate thereof and gelatin, wherein the gelatin is a hydrolyzed gelatin non-gelling at room temperature having a mean molecular weight between about 3000 to 12000 Daltons and wherein the formulation is obtained by freeze drying the homogeneous aqueous solution and further processing the resulting solid material into said oral pharmaceutical formulation.

2. A formulation as claimed in claim 1 wherein the concentration of gelatin is from about 0.01% to about 30% weight/weight of the aqueous solution.

3. A formulation as claimed in claim 1 wherein the gelatin is hydrolysed Type B gelatin, hydrolysed Type A gelatin or a mixture thereof.

4. An oral pharmaceutical formulation as claimed in claim 1 wherein the formulation comprises a unit dose of calcitonin or conjugate thereof from about 20 to about 600 IU.

5. A homogeneous solution comprising calcitonin or conjugate thereof and the hydrolyzed gelatin, non-gelling at room temperature, having a mean molecular weight between about 3000 to 12000 Daltons.

6. A method for the preparation of the formulation as claimed in claim 1 comprising preparing a homogeneous aqueous solution at room temperature comprising calcitonin or a conjugate thereof and the hydrolyzed gelatin, non-gelling at room temperature having a mean molecular weight between abut 3000 to 12000 Daltons without heating said solution above room temperature and freeze drying the resulting solution.

7. The formulation of claim 1 which can be stored for nine months at a temperature of about 20 to about 30° C. and a relative humidity of about 50% to about 65% and retain at least 90% biologically active calcitonin or conjugate.

* * * * *

UNITED STATES PATENT AND TRADEMARK OFFICE
CERTIFICATE OF CORRECTION

PATENT NO. : 6,352,974 B1 Page 1 of 1
DATED : March 5, 2002
INVENTOR(S) : Matteo Ghirri et al.

It is certified that error appears in the above-identified patent and that said Letters Patent is hereby corrected as shown below:

<u>Column 14,</u>
Line 36, after "solution" insert -- of said pharmaceutical formulation --.

Signed and Sealed this

Eleventh Day of February, 2003

JAMES E. ROGAN
*Director of the United States Patent and Trademark Office*